United States Patent [19]
Lee et al.

[11] Patent Number: 5,827,969
[45] Date of Patent: Oct. 27, 1998

[54] PORTABLE HAND HELD DOPPLER FETAL HEART RATE PROBE WITH SELECTIVE POWER SETTINGS

[75] Inventors: William C. Lee, Orinda; Del D. Fisher, Santa Cruz; Andras Boross, Belmont, all of Calif.

[73] Assignee: MedaSonics, Inc., Newark, Calif.

[21] Appl. No.: 662,049

[22] Filed: Jun. 12, 1996

[51] Int. Cl.⁶ .................................................. A61B 8/06
[52] U.S. Cl. ...................... 73/627; 073/861.25; 600/455
[58] Field of Search .................... 128/661.07, 661.09, 128/698; 073/627, 861.25; 364/413.25, 413.02; 600/453, 455, 446, 457

[56] References Cited

U.S. PATENT DOCUMENTS

| 4,413,629 | 11/1983 | Durley III | 600/453 |
| 4,819,652 | 4/1989 | Micco | 73/861.25 |
| 5,313,947 | 5/1994 | Micco | 600/455 |

*Primary Examiner*—Christine K. Oda
*Attorney, Agent, or Firm*—Fliesler, Dubb, Meyer & Lovejoy

[57] ABSTRACT

A probe in a hand held ultrasonic Doppler fetal heart beat detector and monitoring system comprising a crystal for transmitting ultrasonic energy, a variable power source connected to said crystal for driving the crystal at a selected power setting and a microprocessor for selecting a power setting for the variable power source.

16 Claims, 5 Drawing Sheets

PORTABLE HAND HELD DOPPLER FETAL HEART RATE PROBE WITH SELECTIVE POWER SETTINGS

BACKGROUND OF THE INVENTION

1. Field of the Invention

The present invention generally relates to a portable, hand held probe in a Doppler fetal heart beat detection and monitoring system for detecting the fetal heart beat using Doppler ultrasound techniques in general and more specifically to a method and a probe capable of changing the applied ultrasonic field strength thereby increasing the sensitivity of the probe.

2. Description of the Related Art

The Doppler effect was first described in the 19th century by Christian Doppler, an Austrian scientist from Salzburg. A hand held ultrasonic Doppler fetal heart beat detection and monitoring system includes a probe for detecting the fetal heart beat and for providing an analog signal to a headset and/or to an auxiliary unit (hereinafter referred to as a calculation or Calc. unit). The probe includes one or more crystals that transmits and receives ultrasonic sound waves. In use, the detector is held against the mothers abdomen and directed towards the fetus. The transmitter crystal generates an ultrasonic wave that passes into the mothers body. The transmitted ultrasonic wave is reflected by the movement of the fetal heart as a reflected ultrasonic wave to the receiving crystal. The frequency of reflected ultrasonic wave is changed as a function of the velocity of movement of the fetal heart. This frequency shift is detected and processed by the probe into an analog signal that can be heard as the fetal heart beat through the headset and the speaker in the Calc. unit. The Calc. unit also processes the analog signal to derive a fetal heart rate and displays the same.

A probe 11 having a single energy level transmitter and a detector 51, volume controller 52, power supply 54 and of FIG. 2 is available from MedaSonics, Inc. as Part No. 101-0135-010. A Calc. unit suitable for use with probe 11 is available from MedaSonics, Inc., 47233 Fremont Boulevard, Fremont, Calif. 94538, and is identified as FETAL CALC. SPEAKER/HEART DISPLAY, Part No. 101-0238-010. A headset 10 compatible for use with probe 11 can also be purchased from MedaSonics, Inc., and is identified as HEADSET, Part No. 101-0008-010.

During the later stage of the first trimester and the early stage of the second trimester, the heart of the fetus is so small that the conventional hand held Doppler fetal heart beat detection and monitoring systems encounter difficulty in detecting the fetal heart beat due to the very low level of ultrasonic energy in the reflected ultrasonic wave from the fetal heart.

One approach to this problem was to provide a set of interchangeable probes where each probe emits ultrasound energy at a different ultrasonic frequency to improve the sensitivity of the probe in detecting the fetal heart beat. The disadvantage of this solution is that the user has to have easy and immediate access to the set of probes, the necessity of physically having to change the probes during the examination, the potential of one or more probes being damaged and the increase cost of having more than one probe.

Other approaches have been directed to methods of processing of the reflected ultrasonic wave by the detector in the probe to distinguish the low level fetal heart beat component from the noise component of the reflected ultrasonic waves.

Typically a medium, such as an aqueous based acoustic gel or petroleum based gelatin, is applied to the probe. The medium acts as an acoustic impedance matching interface between the probe and the insonated area, which is the skin surface. Application of the medium to the probe generates unwanted noise, referred to as break noise, which appears as a high amplitude signal component in the output signal of the detector and is heard as a loud sound in the head set or from a speaker in the Calc. unit. Break noise is also generated when the probe is moved across the skin surface causing the probe/medium/skin interface to be broken.

SUMMARY OF THE INVENTION

An object of the present invention is to provide a probe that can detect the fetal heart beat during the late part of the first trimester and the first part of the second trimester of pregnancy.

Another object of the present invention is to provide a portable hand held Doppler fetal heart beat detection and monitoring system that uses only one probe and which has variable power settings for controlling the level ultrasonic energy in the ultrasonic wave being transmitted by the probe thereby increasing the level of reflected ultrasound energy from the fetal heart so as to increase the sensitivity of the probe.

The present invention is a method and a probe in a hand held Doppler fetal heart beat detection and monitoring system for detecting the fetal heart beat and for measuring fetal heart rate. The hand held probe comprises a transmitting crystal, a variable power means for selectively driving the transmitting crystal to produce an ultrasonic wave having various levels of ultrasonic energy and a selection means for selecting the power level of the power means. Specifically, a plurality of power drivers is provided which can be interconnected to drive the transmitting crystal at different power levels. A microcontroller controls the selection of which power drivers are to be used, either singularly or in combination with each other, and monitors one or more buttons on the probe such that the user, by depressing one or more buttons, can cause the power level to be changed.

The reflected ultrasound energy from the fetal heart is proportional to the transmitted ultrasound energy from the detector. The sensitivity or signal to noise ratio of the probe depended, in the first order determination, upon the probe's internal generated noise, reflected ultrasonic noise in the reflected ultrasonic wave received by the receiving crystal, commonly referred to as tissue cluttering, and the strength of reflected ultrasound energy reflected by the fetal heart. It has been found that the ratio of an increase in the transmitted energy of the ultrasonic wave is almost entirely translated into an increase in the sensitivity (signal to noise ratio) of the probe.

BRIEF DESCRIPTION OF THE DRAWINGS

The invention will be described with respect to the particular embodiments therefore and reference will be made to the drawings, in which.

DETAILED DESCRIPTION OF THE INVENTION

Figure 1:
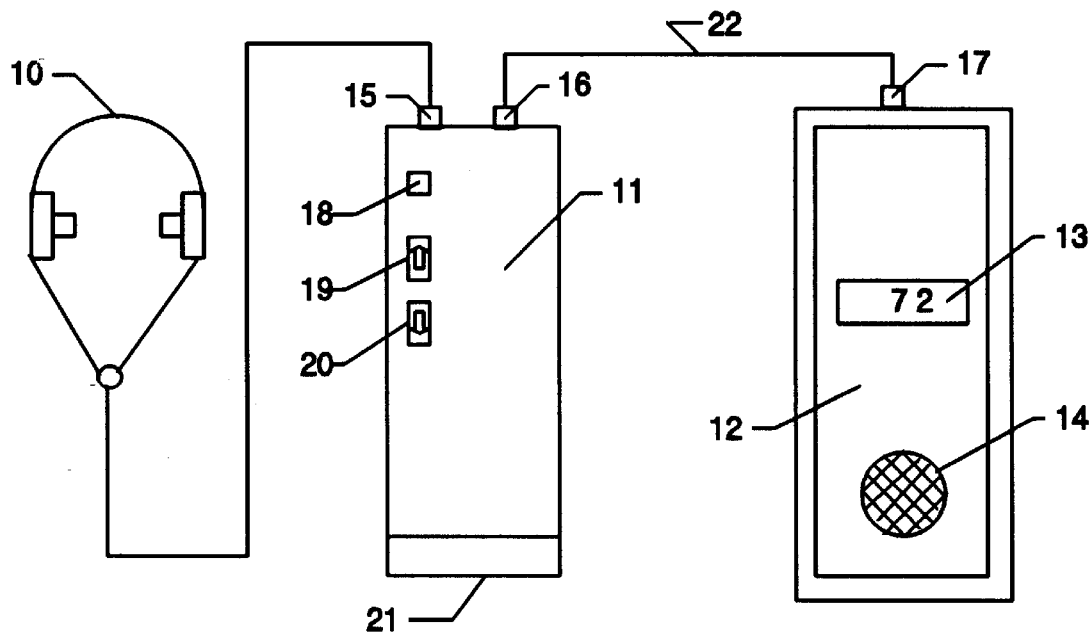
FIG. 1 is an illustration depicting a hand held Doppler fetal heart beat detection and monitoring system including the probe of the invention.

FIG. 1 illustrates an ultrasonic Doppler fetal heart beat detection and monitoring system embodying a probe 11, a head set 10 and a Calc. unit 12. Probe 11 generates ultrasonic waves and then receives and processes reflected ultrasonic waves to generate an analog signal of the fetal heart beat. Probe 11 also includes a power button 18, volume down button 19 and a volume up button 20. The volume level of the sound generated by headset 10 and speaker 14 in Calc. unit 12 is controlled by volume buttons 19 and 20. Crystals that produce and receive ultrasonic waves are located in the base 21 of probe 11. Headset 10 is connected to probe 11 via jack 15 for receiving the analog signal and for generating an audible fetal heart beat. Calc. unit 12 is connected to probe 11 by multi-line cable 22 via plugs 16 and 17 and includes electronic circuitry for processing the analog signal from probe 11 into an audio fetal heart beat which is emitted from speaker 14 and further calculates and displays the fetal heart rate on a display means 13.

A fetal stethoscope is formed by the combination of probe 11 and headset 10 or probe 11 and Calc. unit 12. Headset 10 allows the doctor to solely hear the fetal heart beat during an examination. Calc. unit 12 is used when the doctor wishes the patient to hear the fetal heart beat and/or when the doctor wishes to obtain a read-out on the fetal heart rate.

In use a medium, typically an aqueous based acoustic gel or petroleum based gelatin is applied to base 21 of probe 11. The medium acts as an acoustic impedance matching device to aid in the transmission of ultrasonic waves generated by probe 11 into the body of the mother and in the transmission of reflected ultrasonic waves from the mother, such as the fetal heart, to probe 11. Probe 11 is then placed against the outer skin of the mother with the medium between the probe and the skin. Ultrasonic waves generated by a crystal within probe 11 enters the mothers body. The transmitted ultrasonic waves are reflected by the movement of the fetal heart which changes the frequency of the ultrasonic wave as a function of the velocity of movement of the fetal heart. The energy level of the reflected ultrasonic wave from the fetal heart is directly proportional to the energy level of the transmitted ultrasonic wave from probe 11. The reflected ultrasonic waves pass through the medium and are sensed by a second crystal in probe 11.

It has been found that the energy of other reflected ultrasonic waves from within the mother's body, which is referred to as tissue clutter, is independent of the energy level of ultrasonic waves transmitted by probe 11. Further, the internal noise generated by the electronics within probe 11 is, for the most part, independent of the energy level of ultrasonic waves being generated by crystal 50. A first approximation for the signal to noise ratio of the probe 11 is derived from the magnitude of the noise generated by tissue clutter, the magnitude of the noise generated by the electronics within probe 11 and the magnitude of the energy of the reflected ultrasonic wave from the fetal heart. Therefore an increase in the ultrasonic power in the transmitted ultrasonic wave will increase the signal to noise ratio of the probe in that the energy level of the reflected ultrasonic wave from the fetal heart will be increased while tissue clutter noise and noise generated in the probe will remain at the same level. Tests have shown that by increasing the energy level of the transmitted ultrasonic wave by 6 dB that the signal to noise ratio will be increase by approximately 6 dB.

Figure 2:
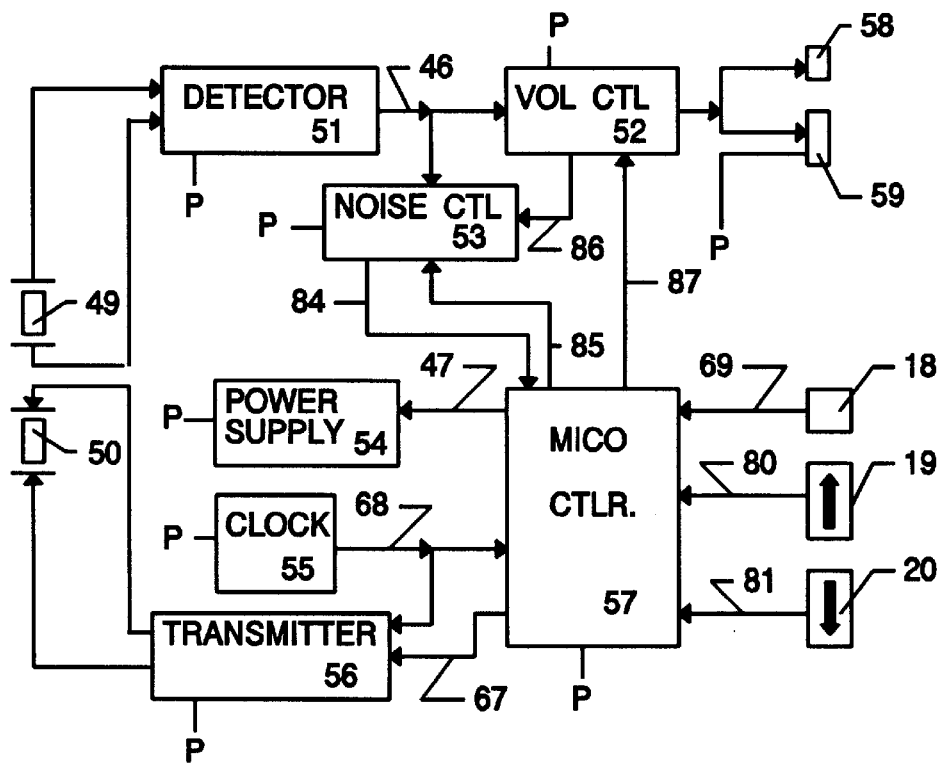
FIG. 2 is a block diagram of the probe of the invention.

FIG. 2 is a block diagram of the major components within probe 11. A transmitter 56 drives crystal 50 at a frequency of the square wave clock signal of clock 55. Microcontroller 57 is commercially available from Microchip Technology, Inc., 2355 West Chandler Blvd, Chandler, Ariz. 85224, as part number PIC 16C622. Microcontroller 57 provides a transmitter power setting signal on bus 67 to transmitter 56 for setting the power level of transmitter 56. Power supply 54 receives a power off signal on line 47 from microcontroller 57 which places microcontroller 57 in a SLEEP state and turns off power to the other components within probe 11. Power supply 54 receives a power on signal on line 47 from microcontroller 57 which places microcontroller 57 in a WAKE state and turns on power to the other components within probe 11. In the SLEEP state, microcontroller 57 monitors power button 18 and upon sensing the depression of power button 18 will send the power on signal to power supply 54.

Receiving crystal 49 responds to the reflected ultrasonic energy in the reflected ultrasonic waves and provides a input signal, derived from the received reflected ultrasonic energy, to detector 51. Detector 51 is well known in the art and examples of detector 51 are provided in Section 14 of the Electronics' Engineers Handbook, Donald G. Fink and Donald Christiansen, McGraw Hill Book Company, 1989, ISSN 0-07-020982-0.

The output signal of detector 51 is provided to a volume controller 52 via line 46 that in turn provides an analog signal at sockets 58 and 59. Socket 58 receives jack 15 from headset 10 and socket 59 receives plug 16 on cable 22 from Calc. unit 12. Socket 59 also provides power from power supply 54 via cable 17 to Calc. unit 12. Microcontroller 57 generates a pulse width modulated signal on line 87 to volume controller 52 for controlling the amplitude of the analog signal generated by volume controller 52. When the volume down button 19 is depressed, the pulse width of the pulse width modulated signal is decreased, thereby causing the amplitude of the analog signal from volume controller 52 to be decreased. Similarly, when the volume up button 20 is depressed, the pulse width of the width modulation signal is increased thereby causing the amplitude of the analog signal from volume controller 52 to be increased.

A noise controller 53 is provided for detecting break noise. Microcontroller 57 monitors the output of noise controller 53 on line 84 and upon sensing break noise being detected by noise controller 53 generates a signal on line 85 to noise controller 53 that activates circuitry within noise controller 53 for reducing the amplitude of the analog signal from volume controller 52.

Figure 3:
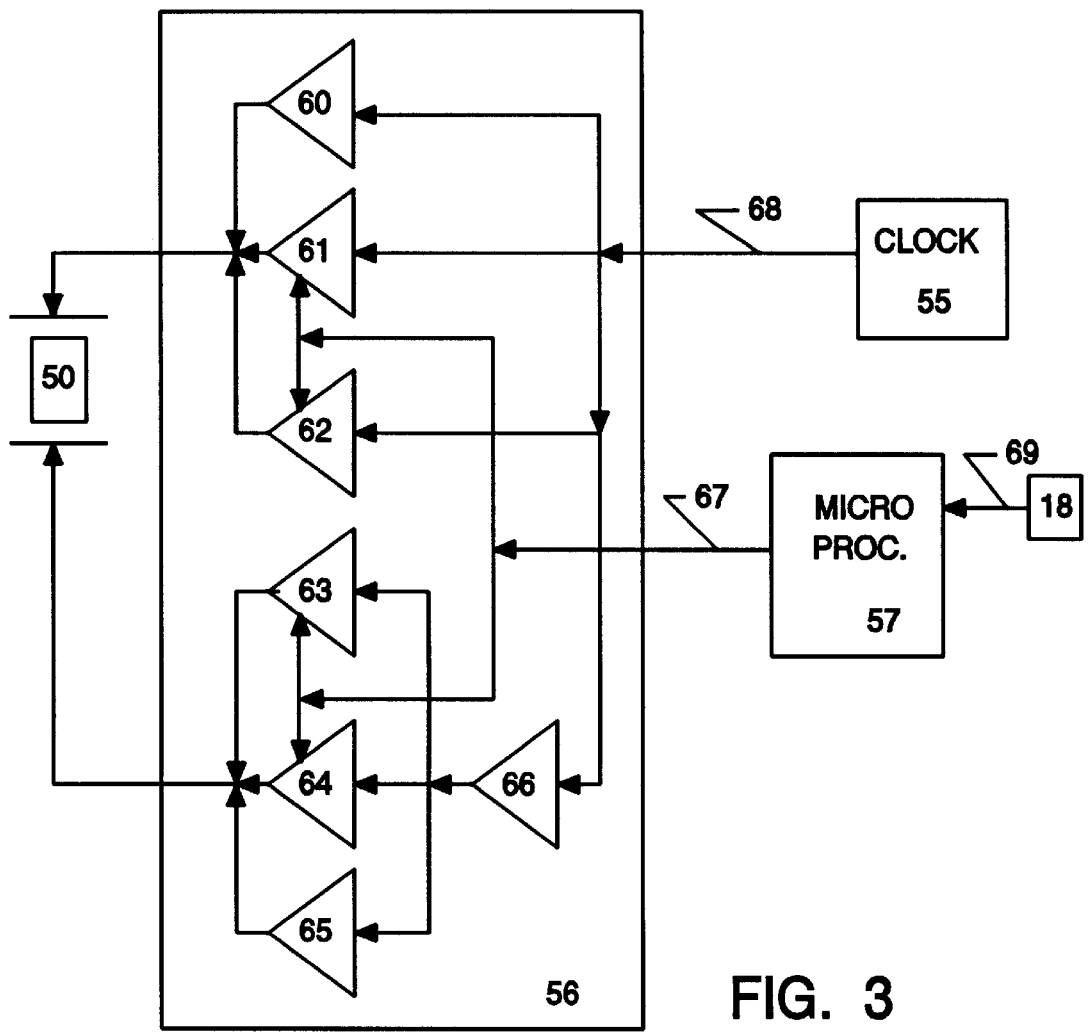
FIG. 3 is a block diagram of a plurality of selective power drivers for driving the transmitting crystal at two different power settings.

FIG. 3 is a block diagram of the transmitting portion of probe 11. Transmitter 56 consists of six power drivers 60, 61, 62, 63, 64 and 65 connected in pairs, where each power drive is an AC or ACT logic tristate inverting buffer. Drivers 60 and 65 are a first pair, drivers 61 and 64 are a second pair, and drivers 62 and 63 are a third pair. Transmitter 56 is a continuous wave (CW) transmitter. Clock 56 provides a square wave clock signal via line 68 to drivers 60, 61 and 62 and to inverter 66 that in turn provides the inverted square wave clock signal to drivers 63, 64 and 65. When power is turned on drivers 60prod 65 are always activated and providing a driving signal to crystal 50. When the square wave clock signal is high driver 60 will act as a current source and driver 65 will act as a current sink and when the square wave clock signal is low driver 60 will act as a current sink and driver 65 will act as a current source. This results in crystal 50 generating an ultrasonic wave at the frequency of the square wave clock signal appearing on line 68 from clock 55. The energy or strength of the ultrasonic wave created by crystal 50 is a function of the magnitude of the power or current driving crystal 50.

Microcontroller 57 monitors the state of power button 18 via line 69. The low power mode is selected by holding down power button 18 for a first period of time and the high power mode is selected by holding down the power button 18 for a second period of time, where the first period is shorter than the second period. When microcontroller 59 determines that power button 18 was depressed for the second period of time for the high power mode, microcontroller 57 conditions drivers 61, 62, 63 and 64 via a signal on line 67. Drivers 61 and 62 are in parallel with driver 60 and drivers 63 and 64 are in parallel with driver 65. When drivers 61, 62, 63 and 64 are activated, the power driving crystal 50 is increased by a factor of four which adds 6 dB to the energy of the ultrasonic wave being transmitted by probe 11.

Figure 4:
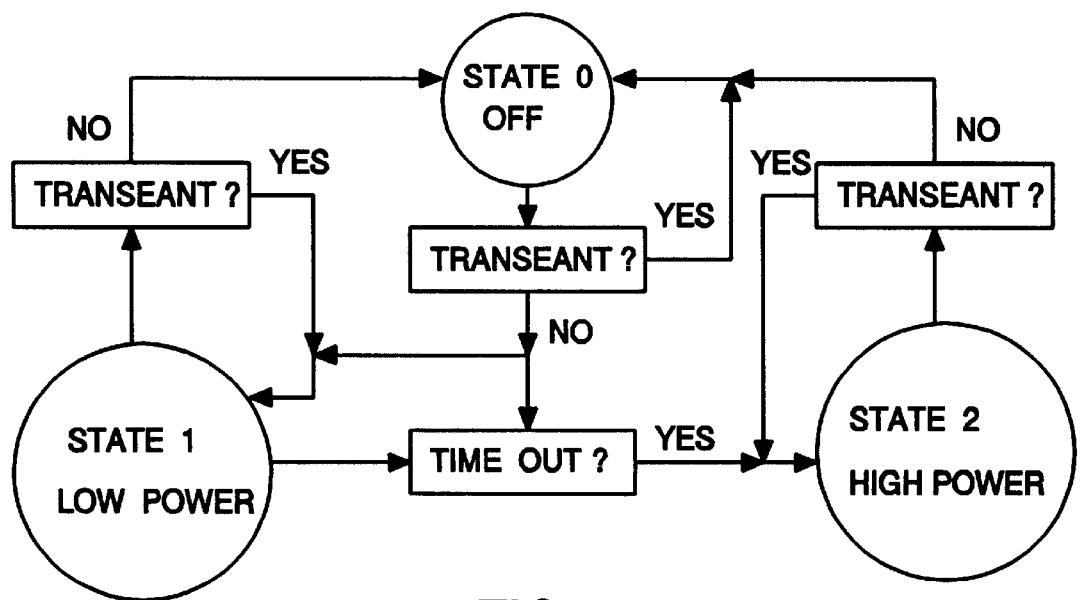
FIG. 4 is a state diagram illustrating the sequence of steps for the selection of one of the two power modes for the probe of the invention.

FIG. 4 is a state diagram illustrating the process that microcontroller 57 follows when monitoring power button 18. Starting with probe 11 in STATE 0, the of f state, when power button 18 is depressed microcontroller 57 will start a timer to assess whether the incoming signal generated by the depressing of power button 18 is a transient signal. Whenever microcontroller 57 determines the occurrence of a transient signal the STATE of probe 11 will not be changed. The remaining discussion will be made assuming that the signal generated by depressing the power button 18, the volume down button 19 and the volume up button 20 is a non transient signal.

When microcontroller 57 determines that signal generated by the depression of power button 18, microcontroller 57 will switch probe 11 to STATE 1, low power state, resulting in crystal 50 being driven only by drivers 60 and 65. The microcontroller 57 will continue to monitor the period that power button 18 is depressed after entering STATE 1 and if the power button 18 has been held down for the second period the microcontroller 57 will switch the probe 11 STATE 1, low power, to STATE 2., high power. This task is accomplished by microcontroller 57 initiating a counter with a count value of the second period when probe 11 is in STATE 0, off state, and power button 18 is first depressed and then counts down that counter for as long as the power button 18 remains depressed. If the counter reaches zero indicating the end of the second period, microcontroller 57 will switch probe 11 from STATE 1, low power, to STATE 2, high power by issuing a signal on line 67 that will turn on drivers 61, 62, 63 and 64 effectively placing drivers 61 and 62 in parallel with driver 60 and drivers 63 and 64 in parallel with driver 65. When drivers 61, 62, 63 and 64 are not in the on state in response to the signal on line 67 from microcontroller 57, the four drivers 61, 62, 63 and 64 are in a high impedance state rather than in an off state. If power button 18 is released prior to the counter reaching zero, then the probe 11 will remain in STATE 1, low power. When probe 11 is in either STATE 1 or STATE 2 and microcontroller 57 again detects that power button 18 is depressed, microcontroller 57 will switch probe 11 to STATE 0, off state.

With this sequence of operation for probe 11, probe 11 can go from the off state to the low power state, or from the off state through the low power state to the high power state. Probe 11 cannot switch between the low power state and the high power state without going through the off state.

Figure 5:
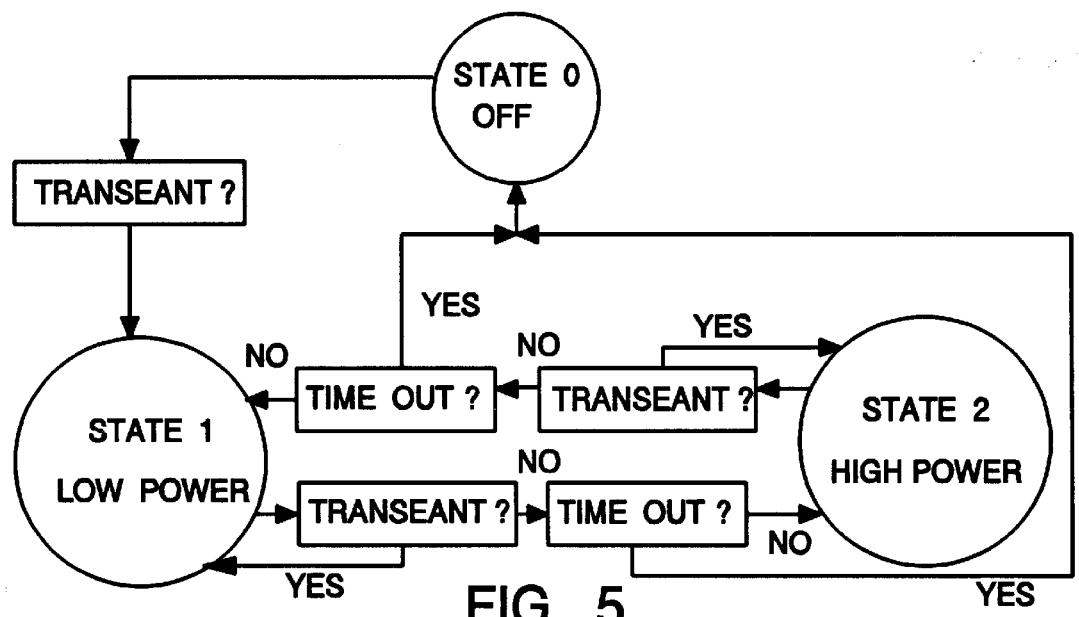
FIG. 5 is a state diagram illustrating another sequence of steps for the selection of one of the two power modes for the probe of the invention.

FIG. 5 is a alternate state diagram illustrating the process that microcontroller 57 follows when monitoring power button 18. Again, assuming that probe 11 is in STATE 0, off state, microcontroller 57 sensing the depressing of power button 18 switches probe 11 from STATE 0 to STATE 1, low power. Upon the next depression of power button 18, microcontroller 57 enters into a time-out phase. Microcontroller 57 loads a counter with a count for recognizing a request for STATE 0, the off state, and counts down the counter as long as the power button 18 is depressed. If the counter does not reach zero before the power button 18 is released then the microcontroller 57 will switch probe 11 from STATE 1, low power, to STATE 2, high power. If the counter reaches zero before the power button 18 is released, then microcontroller 57 will switch probe 11 from STATE 1, low power, to STATE 0, off.

If the probe 11 is in STATE 2, high power, and power button 18 is depressed, microcontroller 57 will enter into the time-out phase. The microcontroller 57 again loads the counter and counts down the counter as long as the power button 18 is depressed. If the counter does not reach zero before the power button 18 is released then the microcontroller 57 will switch probe 11 from STATE 2, high power, to STATE 1, low power. If the counter reaches zero before the power button 18 is released, then microcontroller 57 will switch probe 11 from STATE 2, high power, to STATE 0, off.

With this sequence of operation, probe 11 can switch back and forth between the high power and low power states without first passing through the off state.

Figure 6:
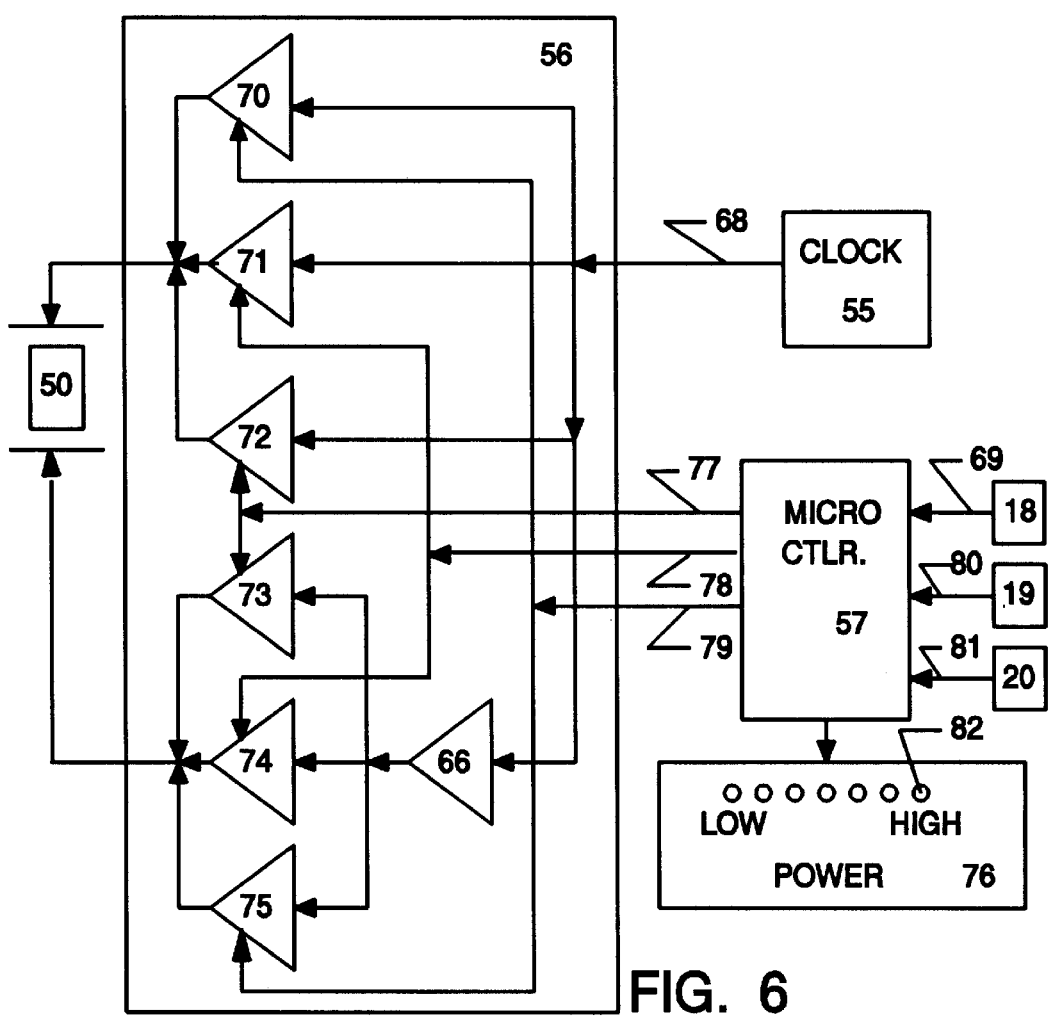
FIG. 6 is a block diagram of a plurality of selective power drivers for driving the transmitting crystal at seven different power settings.

FIG. 6 is an alternate embodiment of the transmitting portion of probe 11. Transmitter 56 is again shown as having six power drivers 70, 71, 72, 73, 74 and 75 connected in pairs where each power driver is an AC or ACT logic tri-state inverting buffer. Drivers 70 and 75 will drive crystal 50 with one unit of ultrasonic energy, drivers 71 and 74 will drive crystal 50 with two units of ultrasonic energy and drivers 72 and 73 will drive crystal 50 with four units of ultrasonic energy. By selecting the power driver pairs that are active, the energy driving crystal 50 can be between one unit and seven units of ultrasonic energy. Again clock 50 produces a square wave clock signal on line 68 connected directly to drivers 70, 71 and 72 and to drivers 73, 74, 75 through inverter 66. Again, when any of the drivers are not selected that driver will be in the high impedance state rather than the off state thereby not causing any loading effect upon crystal 50. Microcontroller 57 selects the power state by monitoring the state of power button 18, via line 69, volume down button 19 via line 80, and volume up button via line 81. A display unit 76 (not shown in FIG. 1) in probe 11 is provided to show the selected power level for probe 11.

Figure 7:
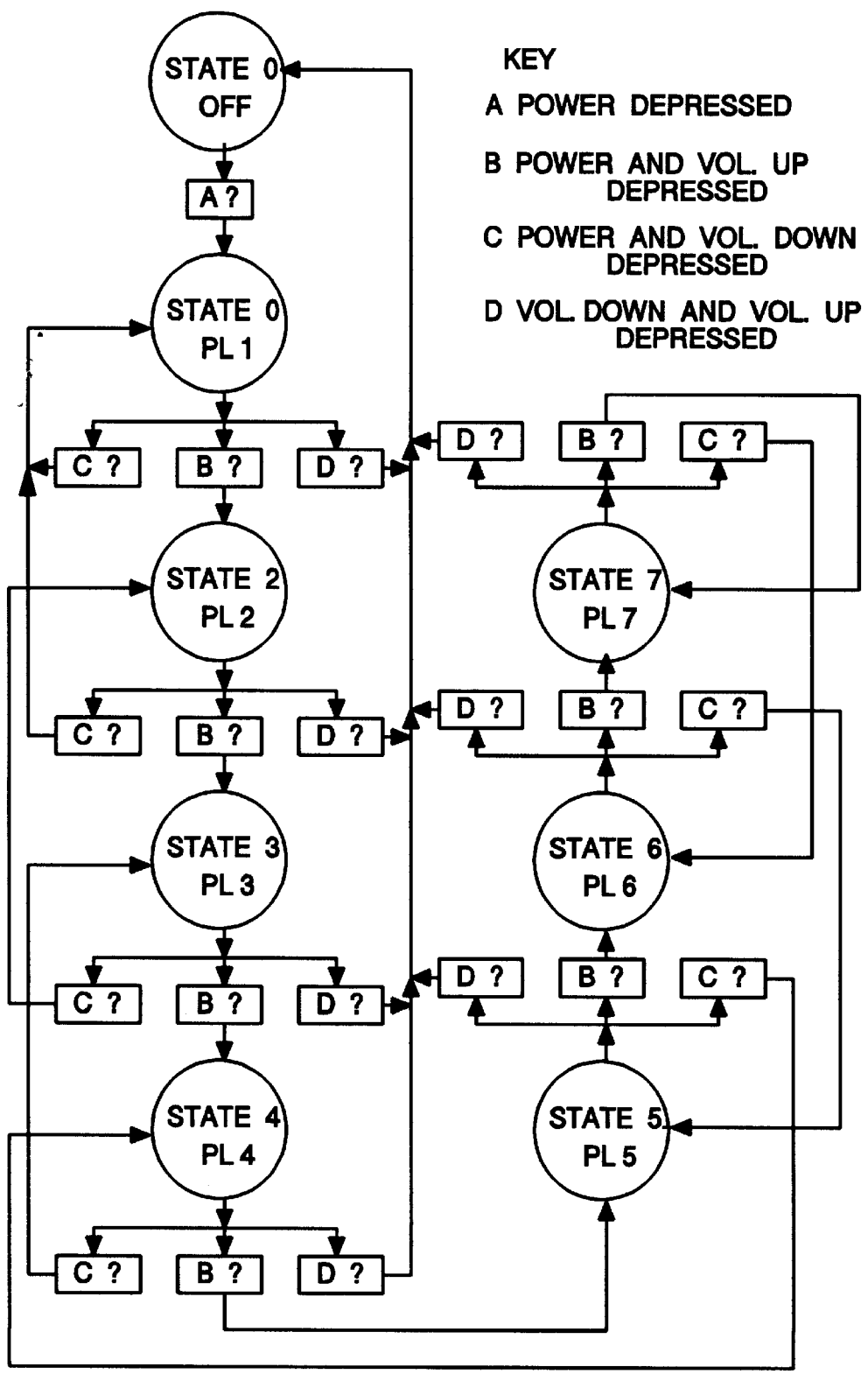
FIG. 7 is a state diagram illustrating the sequence of steps for the selection of one of seven power modes for the probe of the invention.

FIG. 7 is a state diagram for controlling the power level of probe 11 in accordance with commands received via power button 18, volume down button 19 and volume up button 20. In FIG. 7, condition A represents that only power button 18 is depressed; condition B represents that power button 18 and volume up button 20 are simultaneously depressed; condition C represents that power button 18 and volume down button 19 are simultaneously depressed; and condition D represents that volume down button 19 and volume up button 20 are simultaneously depressed.

Again, assume that the microcontroller 57 is in STATE 0, the off state. When microcontroller 57 senses that only the power button 18 is depressed,then microcontroller 57 will switch probe 11 from STATE 0, off, to STATE 1, power level 1. In power level 1 (PL1), microcontroller 57 will initiate a signal on line 19 to turn on drivers 70 and 75 such that crystal 50 is driven with one unit of ultrasonic power. Microcontroller 57 includes a three stage up/down binary counter, which counts from 1 to 7. The count in the up/down counter determines which pairs of drivers are turned by microcontroller 57 via signals on lines 77, 78 and 79. For example, when the up/down counter has a count of five, driver pair 70 and 75 and driver pair 72 and 73 will be turn of thereby by driving crystal 50 with five units of ultrasonic energy.

During Condition B, power button 18 and volume up buttons 20 are simultaneously depressed, the up/down counter will be continuously stepped up to a maximum count of seven or until either the power button 18 or volume up button 20 is released. The rate of stepping the up/down counter is slow enough such that the user, by observing the power indicator, can stop the count at a desired power level PL1–PL7 for probe 11.

During condition C, power button 18 and volume down buttons 19 are simultaneously depressed, the up/down counter will be continuously stepped down to a minimum count of one or until either the power button 18 or volume up button 20 is released. The rate of stepping the up/down counter is slow enough such that the user, by observing the power indicator, can stop the count at a desired power level PL7–PL1 for probe 11.

During condition D, volume up button 20 and volume down button 18 are simultaneously depressed, the microcontroller 57 will switch probe 11 from the present power STATE (PL1–PL7) to STATE 0, off, and reset the up/down counter a binary count of 1.

In this embodiment, the probe 11 can be turned on and off and once tuned on can be stepped up and down between seven power level.

Figure 8:
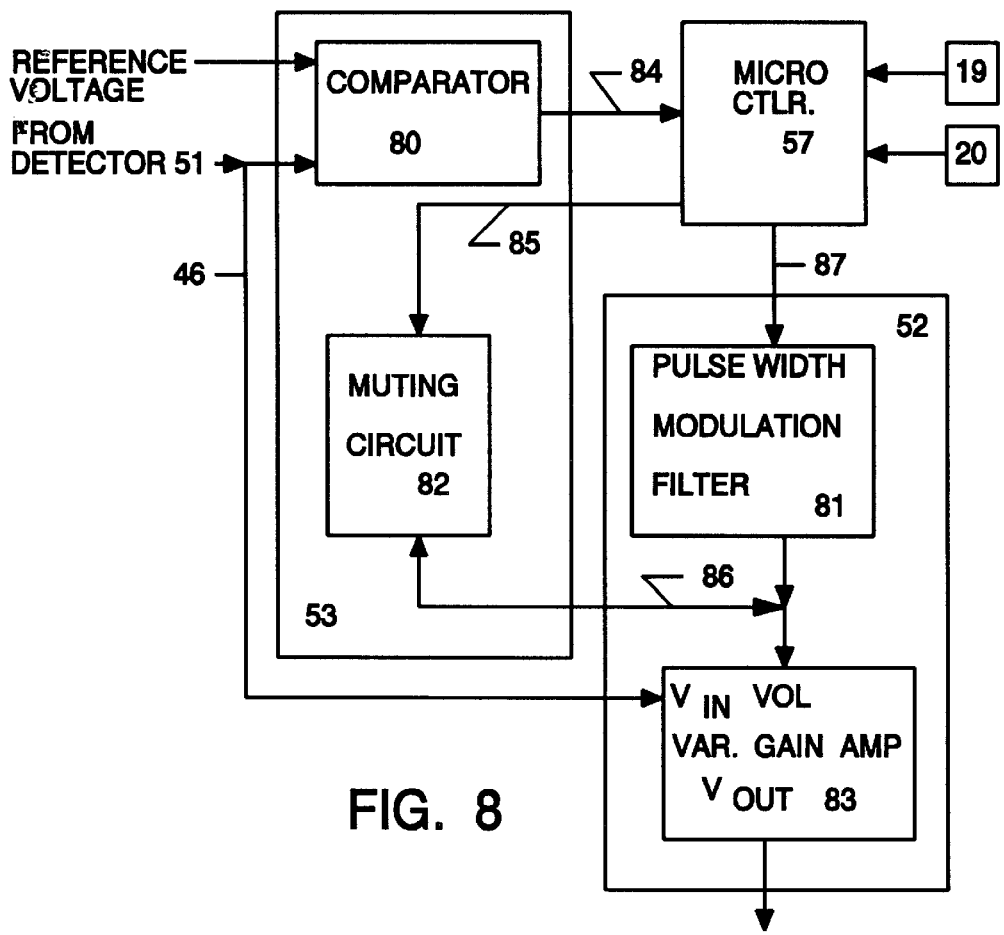
FIG. 8 is a block diagram of the automatic break noise detection and attenuation portion of the probe of the invention.

FIG. 8 is a block diagram of noise controller 53 and the volume controller 52. Noise controller 53 comprises a comparator 18 that monitors the output signal of detector 51 on line 46. The output of comparator 80 will be in a first state whenever the instantaneous magnitude of the output signal from detector 51 is greater than the magnitude of a reference voltage and will be in a second state whenever the instantaneous magnitude of the output signal from detector 51 is less than the magnitude of the reference voltage. As previously stated, break noise is exhibited as a high amplitude signal that is greater in amplitude than the amplitude of the output signal normally expected to be generated by detector 51. Microcontroller 57 monitors the output of comparator 80 and whenever comparator 80 indicates that the output signal from detector 51 is greater than the reference voltage, microcontroller 57 conditions muting circuit 82. Volume controller 52 includes a pulse width modulation filter 81 which generates a gain control voltage on line 86 as a function of the pulse width of the pulse width signal generated by microcontroller 57. Variable gain amplifier 83 gain is controlled by the magnitude of the gain control signal and generates the analog signal provided by probe 11 to headset 10 and Calc. unit 12. Pulse width modulation filter 81 cannot change the gain control voltage fast enough to attenuate the portion of the analog signal associated with the occurrence of break noise in the output signal of detector 51.

Figure 9:
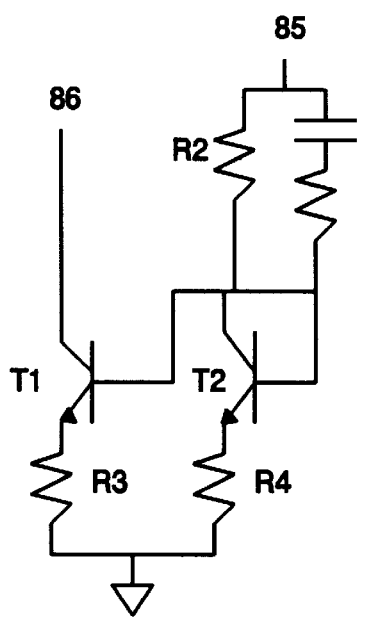
FIG. 9 is a circuit diagram of a current sink circuit of the attenuation portion of the probe of the invention.

FIG. 9 is a circuit diagram of muting circuit 82. Upon detecting the occurrence of break noise, microcontroller 57 generates a voltage on line 85 to muting circuit 82 which effectively, immediately lowers the gain control voltage on line 83 at the output of pulse width modulation filter 81 to variable gain amplifier 83 thereby effectively attenuating the break noise from being emitted through head set 10 or through speaker 14 on Calc. unit 12.

The output of the pulse width modulation filter 81 is connected to the collector of transistor T1 via line 86. When the voltage is placed on line 85, transistor T2 controls the current flow through transistor T1 such that transistor T1 acts as a current sink on the output of pulse width modulator filter 81. The muting circuit of is designed to provide two different levels of attenuation during the attenuation period after break noise is detected. Microcontroller 50 has another timer for timing the time that has elapsed since the last break noise has been detected and maintain the voltage on line 87 to muting circuit 82 until the timer indicates that the attenuation period is over. A typical attenuation period for muting the output signal is 500 ms.

Figure 10:
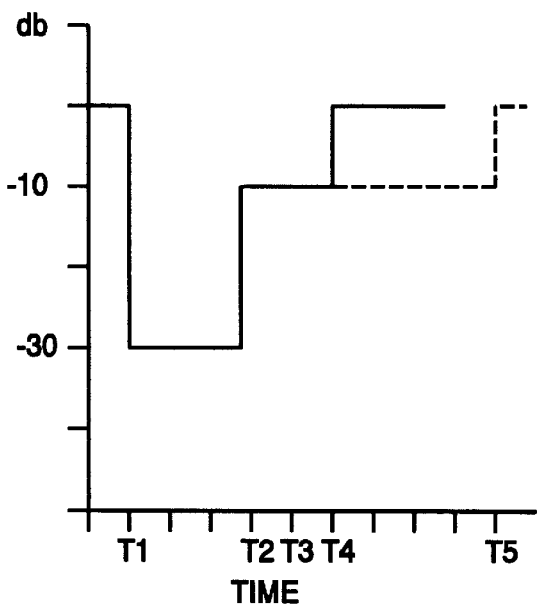
FIG. 10 is a chart illustrating the gain of the variable gain amplifier as a function of the occurrence of break noise is detected.

Referring to FIG. 10, as soon as break noise is detected at T1, the current sink will lower the value of the gain control voltage at the output of the pulse width modulation filter 81 such that the output analog signal of variable gain amplifier 83 will drop by 30 dB. This level of attenuation will change from −30 dB to −10 dB, at time T2, under the control of capacitor C1 and resistor R1. When capacitor C1 is fully charged at T2, the attenuation will be at a level of −10 dB. The period between Ti and T2 is 300 ms. After T2, the attenuation will remain at −10 dB until the timer indicates the end of the attenuation period at T4. Microcontroller 57 will then remove the voltage from the muting circuit, thereby removing the current sink from the output of the pulse width modulator filter 81 and returning the set gain control voltage generated by the pulse width modulation filter 81 to variable gain amplifier 83.

Break noise can occur during an attenuation period. Assume in FIG. 10 that a second occurrence of break noise occurred at time T3. Under this condition the timer for the break noise would be reset for another 500 ms and the attenuation of −10 dB would be held for a full 500 ms until T5 which would be 900 ms after the detection of the first break noise.

While the invention has been particularly shown and described with reference to the preferred embodiments thereof, it will be understood by those skilled in the art that changes in form a detail may be made therein without departing from the spirit and scope of the invention. Given the above disclosure of general concepts and specific embodiments, the scope of the protection sought is defined by the following.

What is claimed is:

1. A probe in a hand held ultrasonic Doppler fetal heart beat detection and monitoring system comprising:
    a crystal for transmitting ultrasonic energy;
    a variable power source, connected to said crystal, having a plurality of power settings for driving said crystal at a selected power setting wherein said variable power source comprises a plurality of pairs of power drivers; and a selection means for selecting a power setting for said variable power source from said plurality of power settings wherein said variable power source comprises a plurality of pairs of power drivers.

2. The probe of claim 1 wherein said selection means selects said power setting in response to user generated power signals.

3. The probe of claim 1 wherein said selection means selects at least a pair of said power drivers in response to a user generated power signal for setting said power setting of said power source.

4. A probe in a hand held ultrasonic Doppler fetal heart beat detection and monitoring system comprising:

a crystal for transmitting ultrasonic energy;

a variable power source, connected to said crystal, having a plurality of power settings for driving said crystal at a selected power setting wherein said variable power source comprises a plurality of cascaded pairs of power drivers where each pair of said power drivers is individually selected; and a selection means for selecting a power setting for said variable power source from said plurality of power settings wherein said variable power source comprises a plurality of pairs of power drivers.

5. The probe of claim 4 wherein said selection means selects at least a pair of said power drivers in response to user generated power signals for setting said power setting of said power source.

6. The probe of claim 5 wherein said selection means comprises:

a POWER button operable by a user for generating said power signals by depressing said POWER button; and a microcontroller for monitoring said POWER button and for selecting a power setting for said power means as a function of when said power button is depressed and the length of time that said POWER button is continuously depressed.

7. The probe of claim 6 has three states of operation, an OFF state, a LOW POWER state and a HIGH POWER state.

8. The probe of claim 7 wherein said microcontroller:

during said OFF state is in a SLEEP state and monitors said POWER button during said SLEEP state and upon detecting a non transient signal generated by depression of said POWER button initiates power to said probe and switching to said LOW POWER state when said POWER button is depressed for a first period of time and to said HIGH POWER state when said POWER button is depressed for a second period of time; and during said LOW POWER state and said HIGH POWER state monitors said POWER button upon detecting a non transient signal generated by depression of said POWER button switches said probe to said OFF state by removing power to said probe.

9. The probe of claim 7 wherein said microprocessor:

during said OFF state is in a SLEEP state and monitors said POWER button during said SLEEP state and upon detecting a non transient signal generated by depression of said POWER button initiates power to said probe and switching to said LOW POWER state when said POWER button is depressed for a first period of time;

during said LOW POWER state upon detecting a non transient signal generated by depression of said POWER button switching to said HIGH POWER state when said POWER button is depressed for said first period of time and to said OFF state when said POWER button is depressed for a second period of time; and during said HIGH POWER state upon detecting a non transient signal generated by depression of said POWER button switching to said LOW POWER state when said POWER button is depressed for said first period of time and to said OFF state when said POWER button is depressed for said second period of time.

10. The probe of claim 5 wherein said selection means comprises:

a POWER button, a VOL UP button and a VOL DOWN button operable by a user for generating said power signals by depressing said POWER button and the combination of any two of said POWER button, said POWER UP button and said POWER DOWN button; and a microprocessor for monitoring said POWER button, said VOL UP button and said VOL DOWN button and for selecting a power setting for said power means as a function of said power signals.

11. The probe of claim 10 wherein said probe has multiple states of operation, an OFF state, a order sequence of POWER states from a LOW POWER state to a HIGH POWER state.

12. The probe of claim 11 wherein said microprocessor:

during said OFF state is in a SLEEP state and monitors said POWER button during said SLEEP state and upon detecting a non transient signal generated by depression of said POWER button initiates power to said probe and switching to said LOW POWER state of said multiple Power states;

during any said multiple POWER state said probe will continuously be stepped to the next higher power state during the period of time that said POWER button and said VOL UP button is simultaneously depressed;

during any said multiple POWER states said probe will continuously be stepped to the next lower power state during the period of time that said POWER button and said VOL DOWN button is simultaneously depressed;

during any said multiple POWER state will switch to said OFF state when said VOL UP button and said VOL DOWN button is simultaneously depressed for a specified period of time.

13. A method of operation for a probe in a hand held ultrasonic Doppler fetal heart beat detection and monitoring system where said probe comprises a crystal for transmitting ultrasonic energy a variable power source connected to said crystal for driving said crystal at a selected power setting, a selection means for selecting a power setting for said variable power source, a POWER button monitored by said selection means, said probe having an OFF state, a LOW POWER state and a HIGH POWER state, said method comprising the steps of:

detecting a non transient signal generated by a first depression of said POWER button;

initiating power to said probe;

first switching to said LOW POWER state from said OFF state when said POWER button is depressed for a first period of time during said first depression of said power button;

second switching to said HIGH POWER state from said LOW POWER state when said POWER button is depressed for a second period of time during said first depression of said POWER button; and third switching from said LOW POWER state and said HIGH POWER state to said OFF state when said POWER button is next depressed after said first depression of said POWER button.

14. The method of claim 13 wherein:

said step of first switching switches said probe to said LOW POWER state from said OFF state when said power button is first depressed and said probe is in said OFF state;

said step of second switching switches said probe to said HIGH POWER state from said LOW POWER state when said POWER button is depressed for a first period of time and said probe in said LOW POWER state;

said step of second switching further switches said probe to said LOW POWER state from said HIGH POWER state when said POWER button is depressed for said first period of time and said probe is in said HIGH power state; and said step of third switching switches said probe from said LOW POWER state and from said HIGH POWER state to said OFF state when said POWER button is depressed for a second period of time where said second period of time is of a longer duration than said first period of time.

15. The method of claim 13, where said monitoring means of said probe monitors said POWER button, a VOL UP button and a VOL DOWN button to select a power state from a sequence of MULTIPLE POWER states which includes said LOW POWER state and said HIGH POWER state, wherein:

said step of first switching switches said probe to said LOW POWER state which is the lowest power state of said MULTIPLE POWER states when power is first initiated to said probe;

said step of second switching switches said probe to a selected higher power state by sequentially stepping up through said MULTIPLE POWER states during the period of time that said POWER button and said VOL. UP button are simultaneously depressed;

said step of second switching further switches said probe to a selected lower power state by sequentially stepping down through said MULTIPLE POWER states during the period of time that said POWER button and said VOL. DOWN button are simultaneously depressed; and said step of second switching switches said probe to the said OFF state from any of said MULTIPLE POWER states when said VOL UP button and said VOL DOWN button are simultaneously depressed.

16. The method of claim 15 further comprising the step of:

displaying the POWER state of said MULTIPLE POWER states presently selected.

* * * * *